(12) United States Patent
Addis et al.

(10) Patent No.: US 10,553,305 B2
(45) Date of Patent: Feb. 4, 2020

(54) DYNAMIC SETUP CONFIGURATOR FOR AN ELECTRONIC HEALTH RECORDS SYSTEM

(71) Applicant: Allscripts Software, LLC, Raleigh, NC (US)

(72) Inventors: David Addis, Oakland, CA (US); Killian Escobedo, San Francisco, CA (US); Richard W. Weldon, San Francisco, CA (US); Sabas Rodriguez, Berkeley, CA (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 0 days.

(21) Appl. No.: 14/311,652

(22) Filed: Jun. 23, 2014

(65) Prior Publication Data
US 2015/0370968 A1    Dec. 24, 2015

(51) Int. Cl.
*G16H 10/60*        (2018.01)
(52) U.S. Cl.
CPC .................................. *G16H 10/60* (2018.01)
(58) Field of Classification Search
CPC .............................................. G06Q 50/22–24
See application file for complete search history.

(56) References Cited

U.S. PATENT DOCUMENTS

| | | | |
|---|---|---|---|
| 2004/0172294 A1* | 9/2004 | Dahlin | G06Q 10/0633 705/2 |
| 2006/0287890 A1* | 12/2006 | Stead | G16H 10/60 705/3 |
| 2007/0168223 A1* | 7/2007 | Fors et al. | 705/2 |
| 2011/0041077 A1* | 2/2011 | Reiner | 715/745 |
| 2013/0061259 A1* | 3/2013 | Raman | H04H 60/32 725/14 |
| 2013/0144816 A1* | 6/2013 | Smith | G06F 19/3443 706/12 |

* cited by examiner

*Primary Examiner* — Robert A Sorey
(74) *Attorney, Agent, or Firm* — Medley, Behrens & Lewis, LLC

(57) ABSTRACT

In an embodiment, a computer-implemented method presents a dynamically configured electronic health record system. In the method, registration information associated with a medical service provider is received for registering with an electronic health record system. A rules database is queried for a rule associated with the received registration information. Based on the rule, configuration information for the provider is generated and a user interface is transmitted to the provider based on the configuration information.

20 Claims, 8 Drawing Sheets

| Scheduled Recently seen | | | |
|---|---|---|---|
| 4 Sceduled patients Tuesday, Dec 13th | | | Actions ⌄ |
| Search using first, last name, SS#, Med ID or DOB 🔍 | | | Add new patient |
| PATIENT/CC | AGE, GENDER/DOB | LAST ENCOUNTER/DX | APPT/STATUS |
| Sarah Williams<br>Panic attacks | 29 Female<br>Feb 5, 1984 | March 16, 2012<br>Diabetes, Hypertension | 9:00 AM<br>In room 3 |
| Elsa Warwick-Freude<br>First time patient | 75 Female<br>Feb 5, 1938 | No record in Practice Fusion | 9:30 AM |
| Mark Han<br>Fever | 61 Male<br>May 12, 1952 | August 3, 2009<br>GERD | |
| Anna Thompson<br>Migraines | 32 Female<br>Dec 20, 1981 | May 21, 2012<br>Annual check-up | |

This is a list of patients with upcoming appointments

Click one of the test patients to begin charting an office encounter

1/9

436

Questions about your Meaningful Use Dashboard?
Check out the Practice Fusion Meaningful Use Center  Learn more Home
Schedule [03]
Tasks [3]
Charts
Messages [12]
Reports
Settings
Help
Feedback
Lock

400

Practice Dashboard

Show... | + | Search 🔍

Actions ˅

👥 Your EHR users
Your EHR system will improve with more users
3/5 Users invited
[Add your users]

✓ Tasks
13 tasks due
3 Encounters need signing
1 Prescription needs renewal
2 new appointmnet requests
View all tasks

Monday, August 21
21 appointments today
Elowin Murdock   8:15am
Jeffrey De Wolk  8:30am
Davis Holmes     8:45am
View schedule

↪ 5 unread messages
Dr. Epstein | Can you fit a pat.
Amanda, RN | Mr. Jones is com...
Amanda, RN | Yes, I'll do it.
view all messages

📊 Meaningful use progress
5/13 Core measures satisfied
2/8 Menu measures satisfied

▸ EHR 101
3 new tutorials
1 Prescription needs renewal
2 new appointment requests
5 new lab results
View all tutorials Home | Schedule | Tasks | Charts | Messages | Reports | Settings | Log off Questions about your Meaningful Use Dashboard?
Check out the Practice Fusion Meaningful Use Center [Learn more]

Help | Feedback       Jeff Dewalt | Unknown facility

DYNAMIC SETUP CONFIGURATOR FOR AN ELECTRONIC HEALTH RECORDS SYSTEM

BACKGROUND

Field

This application is generally related to configuring an electronic health record system.

Background

Electronic Health Records

Medical records related to a patient's health information are essential to the practice of medical care. Originally, medical records were paper-based documents. The emergence of electronic medical record systems (EMR), which are digital version of previously paper charts that contain a patient's medical history from one medical practice, offers medical professionals and patients with new functionalities and efficiencies that paper-based medical records cannot provide. An electronic health record (EHR), also known as an electronic medical record (EMR), is a collection of electronically stored information about an individual patient's medical history. EHRs may contain a broad range of data, including demographics, medical history, medication history, allergies, immunization records, laboratory test results, radiology images, vital signs, personal statistics like age and weight, and billing and insurance information. Many commercial EHR systems combine data from a number of health care services and providers, such as clinical care facilities, laboratories, radiology centers, and pharmacies.

EHRs are a dramatic improvement over paper-based medical records. Paper-based medical records require a large amount of physical storage space. Paper records are often stored in different locations, and different medical professionals may each have different and incomplete records about the same patient. Obtaining paper records from multiple locations for review by a health care provider can be time consuming, complicated, and sometimes impossible. In contrast, EHR data is stored in a digital format, and thus are more secure and can be accessed from anywhere. EHR systems significantly simplify the records review process for health care providers. Because records in EHRs can be linked, EHRs vastly improve the accessibility of health records and the coordination of medical care.

EHRs also decrease the risk of misreading errors by health care professionals. Poor legibility is often associated with handwritten, paper medical records, which can lead to medical errors. EHRs, on the other hand, are inherently more legible given that they are typically stored in legible typography. In addition, electronic medical records enhance the standardization of forms, terminology and abbreviations, and data input, which help ensure the reliability of medical records, and standardization of codesets. The storage of EHR data means that data from different information systems, including, but not limited to EHR systems, can be displayed in a single, unified record. Further, a patient's EHR record can be transferred electronically, thus reducing delays and errors in recording prescriptions or communicating laboratory test results.

The benefits of digitizing health records are substantial. Health care providers with EHR systems have reported better outcomes, fewer complications, lower costs, and fewer malpractice claim payments. But despite EHRs' potential in drastically improving the quality of medical care, a significant number of health care providers still do not use EHR systems. While the advantages of EHRs are significant, they also carry concerns, including high costs, lost productivity during implementation or computer downtime, and poor EHR usability.

The Health Insurance Portability and Accountability Act (HIPAA), enacted in the U.S. in 1996, and as amended, established rules for use and access of protected health information (PHI). HIPAA provides restrictions on disclosure of and access to protected health information to and by third parties. HIPAA applies to information in electronic medical records, such as the health information doctors and nurses input, documented conversations between a doctor and a patient, and information used to process or facilitate medical billing claims and documents. The HIPAA Security Rule, effective on Apr. 20, 2005 for most covered entities, adds additional constraints to electronic data security and the storage and transmission of PHI.

The high cost of most EHRs also significantly hinders EHR adoption. A large number of physicians without EHRs have referred to initial capital costs as a barrier to adopting EHR systems. Cost concerns are even more severe for smaller health care facilities, because current EHR systems are more likely to provide cost savings for large integrated institutions than for small physician offices. During the EHR technology's setup and implementation process, productivity loss can further offset efficiency gains. The need to increase the size of information technology staff to maintain the system adds even more costs to EHR usages.

Usability is another major factor that holds back adoption of EHRs. It is particularly challenging to develop user-friendly EHR systems. There is a wide range of data that needs to be integrated and connected. Complex information and analysis needs vary from setting to setting, among health care provider groups, and from function to function within a health care provider group. To some providers, using electronic medical records can be tedious and time consuming, and the complexity of some EHR systems renders the EHR usage less helpful. Some doctors and nurses also complain about the difficulty and the length of time to enter patients' health information into the system.

Under-utilization of EHR systems, despite incentives and mandates from the government and the tremendous potential of EHRs in revolutionizing the health care system, calls for better EHR systems that are secure, cost-effective, efficient, well-designed, and user-friendly.

Comprehensive EHR systems can provide capabilities far beyond simply storing patients' medical records. Because EHR systems offer health care providers and their staff the ability to securely store and utilize structured health information, EHR systems can have a profound impact on the quality of the health care system. In Framework for Strategic Action on Health Information Technology, published on Jul. 21, 2004, the Department of Health & Human Services (HHS) outlined many purposes for EHR services. The outlined purposes include, among other things, improving health care outcomes and reducing costs, reducing record-keeping and duplication burdens, improving resource utilization, care coordination, active quality and health status monitoring, reducing treatment variability, and promoting patients' engagement in and ownership over their own health care.

Recent legislation has set goals and committed significant resources for health information technology (IT). One of the many initiatives of the American Recovery and Reinvestment Act of 2009 (ARRA) was "to increase economic efficiency by spurring technological advances in science and health." The Health Information Technology for Economic and Clinical Health (HITECH) Act, passed as a part of ARRA, allocated billions of dollars for health care providers to adopt and meaningfully use EHRs in their practices. HITECH also mandates the Office of the National Coordinator for Health Information Technology (ONC) to define certification criteria for "Certified EHR Technology."

EHR systems satisfying "Certified EHR Technology" criteria are capable of performing a wide range of functions, including: entry and storage, transmission and receipt of care summaries, clinical decision support, patient lists and education resources, generation of public health submission data, and patient engagement tools. Entry and storage is related to the ability to enter, access and modify patient demographic information, vital signs, smoking status, medications, clinical and radiology laboratory orders and results. Transmission and receipt of care summaries involve the ability to receive, incorporate, display and transmit transition of care/referral summaries. Clinical decision support features configurable clinical decision support tools, including evidence-based support interventions, linked referential clinical decision support, and drug-drug and drug-allergy interaction checks. Patient lists and education resources include the ability to create patient lists based on problems, medications, medication allergies, demographics and laboratory test result values, and the ability to identify patient-specific education resources based on such data elements. Generating public health submission data allows users to create electronic immunization and syndromic surveillance data files that can be submitted to public health agencies. Patient engagement tools allow medical professionals to grant patients with an online means to view, download and transmit their health information to a third party, provide patients with clinical summaries after office visits, and facilitate secure-doctor patient messaging.

Usability

Usability is a major factor that has delayed adoption of EHRs. Practices use a wide range of record-keeping systems, and switching to a completely different record-keeping system is non-trivial. A practice may be completely paper-based or use an unfamiliar electronic system, and therefore users may need substantial training to become proficient at using a new EHR. Time constraints and a high volume of patients in certain practices may further exacerbate the cost of learning to use a new EHR. Moreover, while some practices may need many of the available tools and services, others may need only a few, and may be burdened by the complexity of unnecessary features.

BRIEF SUMMARY

Accordingly, it would be advantageous to provide an EHR system that dynamically and easily configures an EHR interface based on the needs of a provider.

In an embodiment, a computer-implemented method presents a dynamically configured electronic health record system. In the method, registration information associated with a medical service provider is received for registering with an electronic health record system. A rules system is queried for a rule associated with the received registration information. Based on the rules, configuration information for the provider is generated and a user interface is transmitted to the provider based on that configuration information.

Method and computer program product embodiments are also disclosed.

Further embodiments, features, and advantages of the invention, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable a person skilled in the relevant art to make and use the disclosure.

FIGS. 4A-D are screen layouts of a user interface generated using a dynamic setup configurator, according to an example embodiment.

The drawing in which an element first appears is typically indicated by the leftmost digit or digits in the corresponding reference number. In the drawings, like reference numbers may indicate identical or functionally similar elements.

DETAILED DESCRIPTION

Overview

Transitioning to an electronic health record (EHR) system can be an overwhelming task for many medical providers. Individual doctor's practices can have dramatically different needs depending on their size, medical specialty, patient population or other particular circumstances. As a result, it is difficult to provide a single EHR solution that can work for various medical providers. For that reason, providers may have to perform substantial customization and configuration of their EHR system to obtain its full benefits and to determine if the system meets their needs.

To facilitate the configuration of an EHR system, embodiments provide a dynamic setup configurator that provides suggestions to a user and configures the interface based on a provider's registration information, typical usage characteristics of similar providers, and detected usage patterns associated with users of the EHR system.

System Overview

Figure 1:
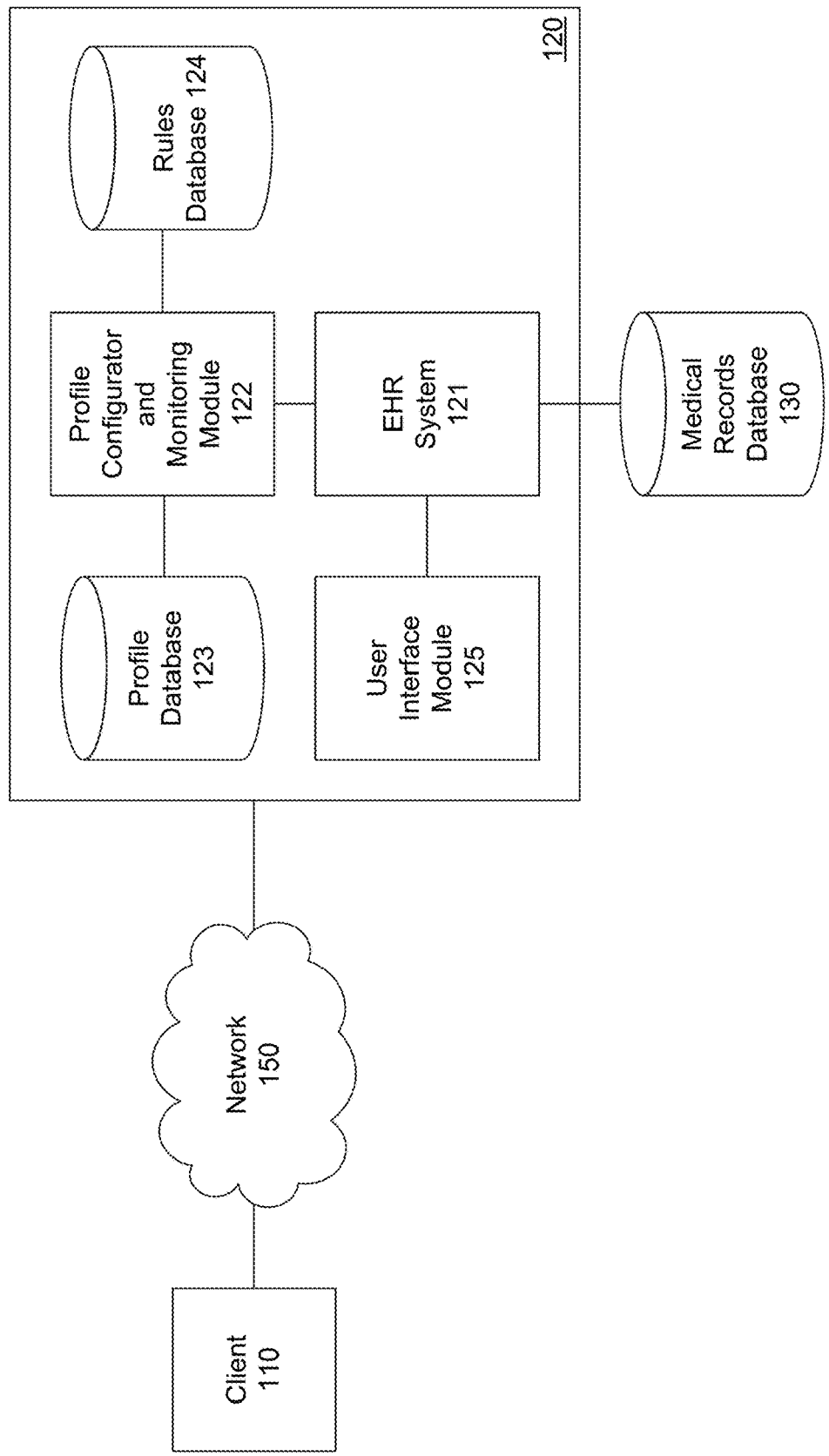
FIG. 1 is a diagram illustrating an example system for providing a dynamic setup configurator to an EHR, according to an example embodiment.

FIG. 1 shows a diagram illustrating an example system 100 for providing a dynamic setup configurator to an EHR, according to an example embodiment. System 100 includes an EHR client 110 and an EHR server 120 connected by one or more networks 150, such as the Internet. Server 120 is also coupled to a medical records database 130. Server 110 may be part of a comprehensive EHR system, as described in further detail below.

Client 110 may, for example, include a web browser that enables a user to interact with an EHR system. The web browser responds to user input, such as user selection of different portions of an interface, by sending an HTTP request to server 120 via network 150. In another example, the user may interface with client 110 through a native application instead of a web browser, and the native application may communicate with server 120. Client 110 may be any type of computing device, such as and without limitation, a PC, laptop, or mobile device.

EHR server 120 may be any computing device configured to provide an EHR system interface and functionality. For example, EHR server 120 can be a computing device as described below with reference to FIG. 5.

Medical records database 130 may be any computing device configured to maintain and provide access to medical records and other patient information. For example, medical records database 130 may be a commercially available or proprietary relational database. EHR server 120 and medical records database 130 may be hosted on the same or separate computing devices.

Client 110 initially interacts with EHR server 120 by initiating a medical practice registration process. The practice registration process may be initiated by a user interacting with an EHR interface provided by server 120 and displayed in client 110. During the practice registration process, client 110 provides information regarding the medical practice, such as, by way of example and not limitation, identifying information, location, types of insurance accepted, number of practitioners in the practice, practice specialties, procedures performed, number of patients, patient types, etc.

During or after the practice registration process, users can also create personal profiles associated with a practice. For example, every doctor, nurse, technician, office staff, and biller in the practice may create their own individual profiles. Server 120 stores the registration information for the practice and one or more user profiles associated with each practice. Users can then log in to the EHR system through their user profile.

During user profile creation, EHR server 120 may request additional information from client 110. The additional information request may be based on the registration information. For example, if the practice is an internal medicine practice, server 120 may ask client 110 whether the doctor performs ambulatory surgery. EHR server 120 can use the practice registration information and the additional requested information to determine a configuration for each user profile, and then provide an EHR interface and services based on this configuration. For example, if the practice registration information ising:
medications, server 120 can configure user profiles to enable e-prescription or lab service connections that enable users to perform these tasks and use these functionalities within their EHR account.

Once client 110 begins its interaction with the EHR system, server 120 can monitor the activity of users to further tailor the interface and services provided. For example, server 120 can detect that a user is querying for information about a patient's medication. Based on this activity, server 120 can send a message to client 110 suggesting that the user enroll in an electronic prescription service offered by server 120, and prompting the user for a response. Additionally, server 120 can monitor underlying patient medical records and suggest interface and services based on the records. For example, server 120 can detect that the medical practice has several patients that routinely undergo laboratory tests, and based on this can send a message to client 110 suggesting that the user enroll in an electronic laboratory service.

In the embodiment of FIG. 1, server 120 includes five modules: EHR system module 121, configurator module 122, profile database 123, rules database 124, and user interface module 125. Each module is described below in turn.

EHR system module 121 implements the functionality of an EHR system. For example, EHR system module may store medical records, transmit and receive medical care summaries, provide clinical decision support information, maintain patient lists and education resources, generate public health submission data, etc. EHR system module 121 may communicate through network 150 with other entities, for example, pharmacies, other EHR systems, laboratories, imaging centers, consumer health devices, databases, etc., to perform EHR tasks.

EHR system module 121 communicates with client 110 through network 150 using a user interface module 125. User interface module 125 generates a graphical user interface (GUI) based on commands from EHR system module 121. In an embodiment, user interface module 125 generates a web-based GUI for display in client 110. A user of client 110 can then interact with the GUI and transmit commands to EHR system module 121.

Configurator module 122 obtains information from the rest of the modules and determines configuration parameters and suggestions for client 110. Configurator module 122 can analyze practice information, such as, for example, the practice registration information, data related to the activity of practice user profiles, and additional information requested from users, etc. Configurator module 122 evaluates this practice information against rules and policies to determine an interface configuration that would suit each user profile. Configurator module 122 may configure tutorial task and setup task suggestions for the client 120 to complete in order to improve their EHR experience. For example, configurator module may detect based on the client information that a user profile would benefit from registering for e-prescription and completing an e-prescription tutorial. Configurator module can then configure the user profile to cause the EHR interface to prompt the user to register, complete the tutorial and enable the e-prescribing feature.

Configurator 122 also keeps track of task and tutorial completion by users. Based on the user's task completion status, the EHR interface may display a progress indicator for task. For example, the EHR interface may show a pop-up message indicating that 3 out of 9 steps of a tutorial have been completed, and explaining the next steps towards completing the tutorial.

Configurator module 122 also monitors user activity to further tailor the user's configuration parameters. For example, configurator module may detect that a user is querying database 130 for patient medication records. In response to detecting that a doctor is looking at medication information, configurator 122 may configure EHR system 121 to offer the user to subscribe to an e-prescription service and take a tutorial on using e-prescription.

Profile database 123 contains user profile information associated with medical practices registered with EHR system 121. When a new user profile is created, EHR system module 121 stores the profile information in profile database 123. Profile database 123 also contains configuration information associated with each profile. Profile configuration information can be set by EHR system 121 based on user preferences, and by configurator 122 based on rules, policies and user activity monitoring.

Rules database 124 contains rules and policies that configurator module 122 can use to determine appropriate configurations and suggestions for users. These rules and policies can map practice information and user profile information to particular services, suggestions or tutorial recommendations. For example, a rule may specify that if a user profile is associated with an accountant, configurator module 122 configures the user profile to display a billing interface, to prompt the client to register for e-billing, and to take a series of e-billing tutorials. Configurator 122 may evaluate rules in rules database 124 in response to receiving registration information or monitoring activity. Configurator 122 may evaluate the information or activity against the rules to determine what configuration changes to perform.

In an embodiment, administrator sets rules of the EHR service based on usage patterns and practical knowledge of the operation of medical practices. In an embodiment, configurator module 122 can generate, modify or add to the rules. For example, rules may be generated based on monitoring of user activity or historical EHR usage patterns by similar doctors or practices. For example, the configurator module 122 may evaluate user activity over a period of time, and determine that dermatologists frequently order laboratory studies to external laboratories. Based on this pattern, configurator module 122 may create a new rule in rules database 124 that triggers e-laboratory setup and training tasks for dermatology practice users.

Additionally, when new EHR services or interface components are added, administrators may add rules that may determine when and how the new services or components are displayed. For example, after an EHR is deployed, EHR developers may add a new component for tracking patient intake documents. The new component may be integrated into the EHR by adding new rules to rules database 124. These new rules may determine which providers receive or are offered the new component. Thus, users may avoid the need to manually reconfigure the EHR to incorporate new components.

Rules may also be derived from global activities and information of multiple practices. In an embodiment, the EHR system may monitor and track trends among practices in a region (country, city, neighborhood, etc.) and compare particular practices with those trends. The EHR system may apply information from several practices to population health management. For example, an EHR system may review vaccination records to keep track of vaccination rates in a region. Rules can then be generated that trigger an alert for providers whose patient vaccination rates are below a determined threshold. The rules may also trigger actions such as suggesting an outreach campaign to encourage vaccination among the patients, and provide resources for implementing such a campaign.

Figure 2:
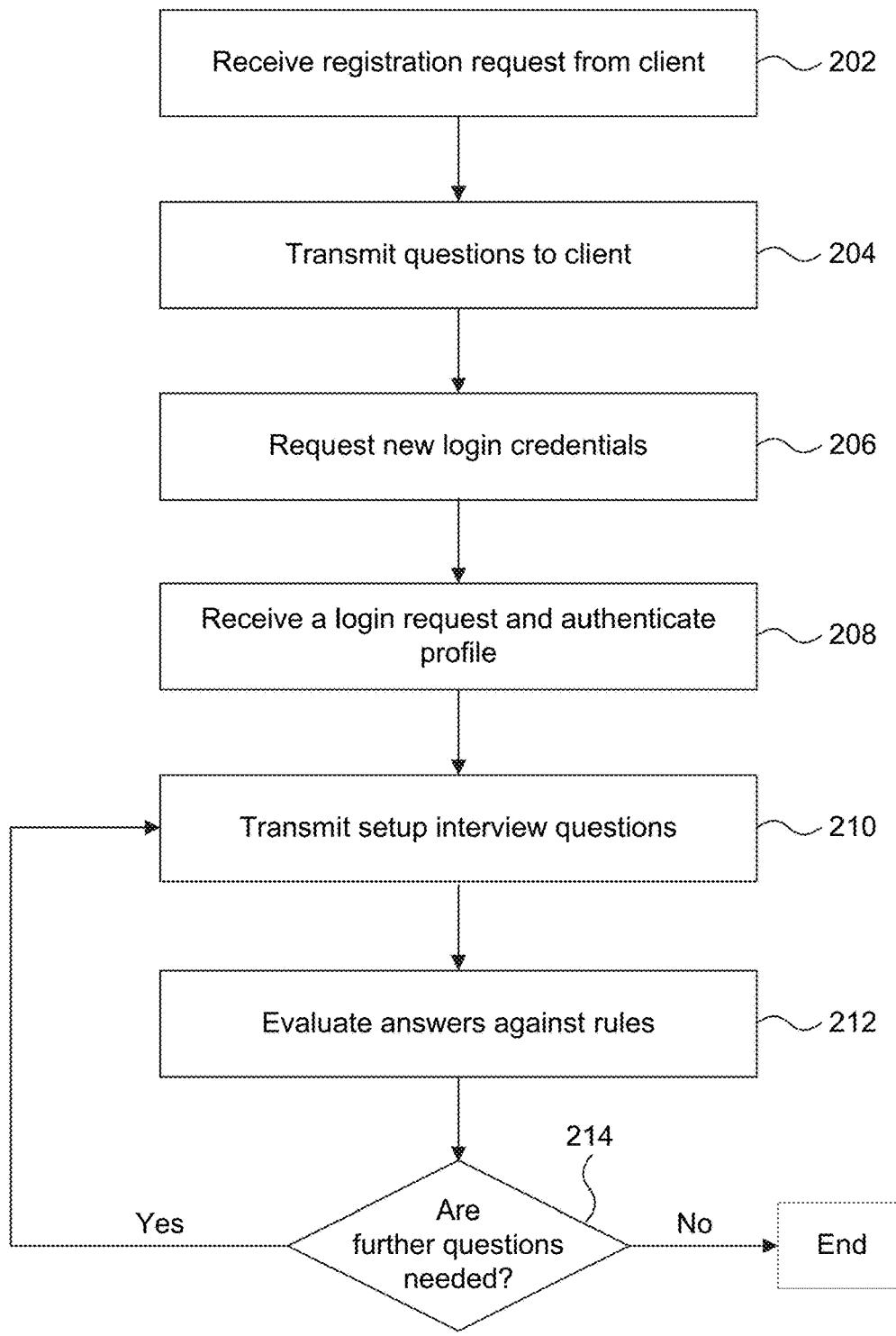
FIG. 2 is a flowchart illustrating an example method for tailoring the configuration of a client profile based on registration and setup information, according to an example embodiment.

FIG. 2 is a flowchart illustrating a method 200 for tailoring the configuration of a client profile based on registration and setup information, according to an example embodiment. As those skilled in the relevant arts will recognize, it is not necessary that all the described steps be performed, or be performed in the order described.

At step 202, an EHR server receives a practice registration request from a client through a network. The request initiates the process of registering a practice for using the EHR system.

At step 204, the EHR server transmits one or more questions or requests for information to the client. For example, the server can request the client for a practice's name, a provider's specialty, and for the role of the user in the practice (e.g., doctor, assistant, nurse, office staff, medical assistant, etc.).

At step 206, the EHR server requests the client to provide new login credentials (e.g., email, username, password) to be associated with a new profile for the user. The EHR server then creates a user profile with those login credentials.

At step 208, the EHR server receives a login request and authenticates the user using the login credentials.

At step 210, the EHR server initiates a setup interview process to determine an appropriate configuration for the user profile. In this step, the EHR server transmits questions to the client and receives answers. The questions can include, for example, questions about the practice's current method of maintaining paper records, a name of a current EHR system the practice is using, how many locations the practice operates, how many people work in the practice, what type of services the practice provides, what billing systems are used, what appointment systems are used, etc.

At steps 212 and 214, the EHR server evaluates the client responses to the questions against a rules or policy engine to determine whether additional questions are needed. For example, if the client indicated that the practice is a cardiology practice, the configurator module in the EHR server may evaluate the cardiology specialty in the rules database and determine that the EHR system should ask the client whether the cardiology practice includes imaging services. If, on the other hand, the practice is a behavioral psychology practice, the system may omit asking about imaging services. In this manner, the questions asked are fine-tuned depending on the previously provided information, and thus the system avoids burdening the user with unnecessary questions that would complicate the setup process.

If at step 214 the EHR server determines that no further questions are needed, it terminates the setup interview and proceeds to create a configuration for the user profile. The EHR server then generates and transmits the EHR user interface for display at the client, based on the user profile configuration.

Figure 3:
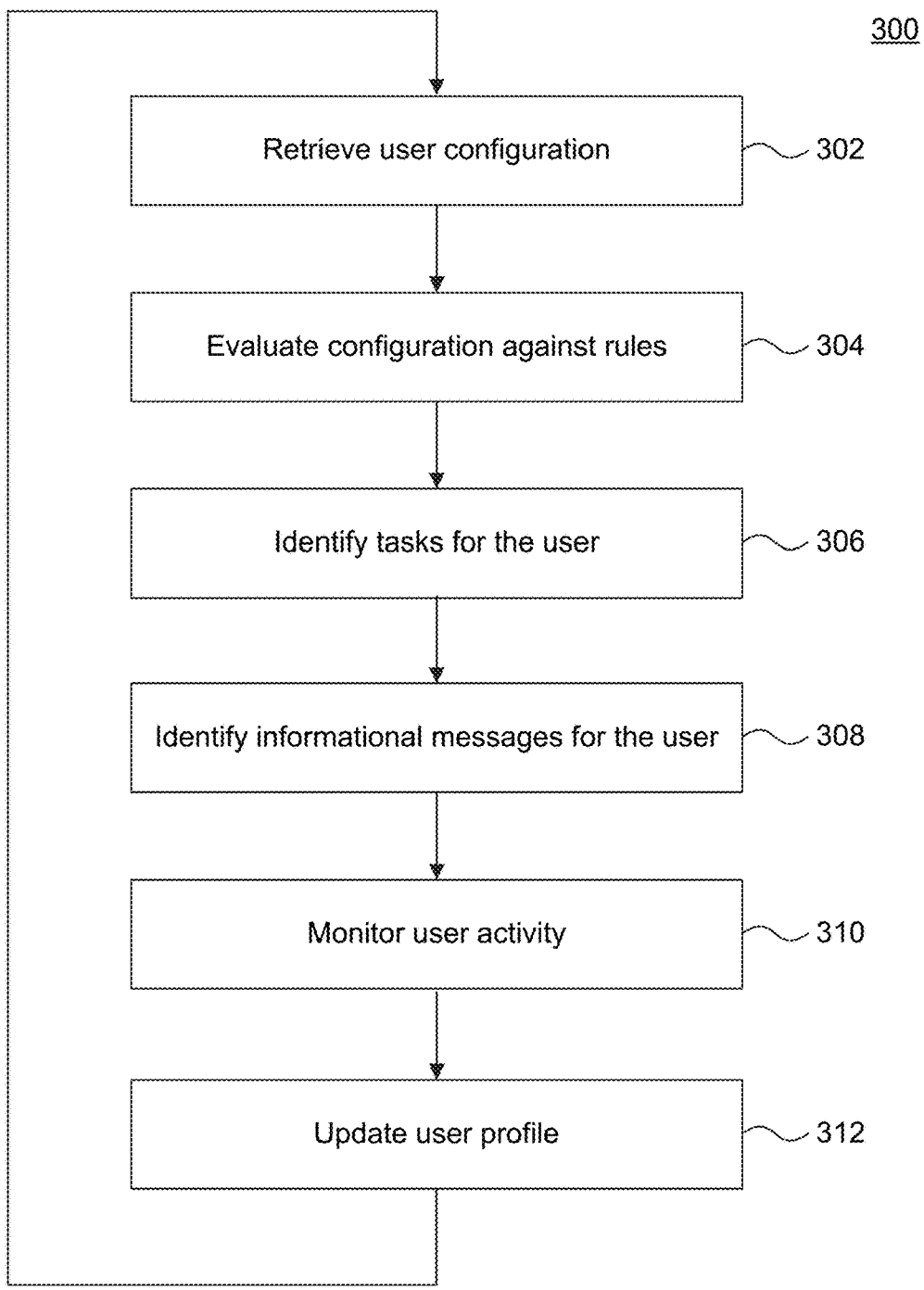
FIG. 3 is a flowchart illustrating an example method for dynamically tailoring the configuration of an EHR user interface based on configuration and user activity, according to an example embodiment.

FIG. 3 is a flowchart illustrating a method 300 for dynamically tailoring the configuration of an EHR user interface based on rules and user activity, according to an example embodiment. As those skilled in the relevant arts will recognize, it is not necessary that all the described steps be performed, or be performed in the order described.

At step 302, the EHR server retrieves the configuration of the user profile associated with a user login.

At step 304, the EHR server evaluates the configuration against the rules and policies in a rules database. As explained, the rules may be updated based on observed trends in the particular practice or global trends among multiple practices or providers.

At step 306, the EHR server identifies suggestions, alerts, or tasks for the user based on the evaluation of the rules. For example, the EHR server may determine that based on the configuration and the rules, the user is likely to need to use e-prescription services. Therefore, the user is provided with a list of tasks associated with e-prescription services, such as, by way of example, registering for e-prescription, completing an e-prescription tutorial, etc. Moreover, if the user is an advanced user and has been using e-prescription for some time, the EHR server may provide a more advanced list of tasks, such as, for example, suggesting tutorials for new services that the user has not taken advantage of yet, such as billing services and imaging center connections.

At step 308, the EHR server also identifies informational messages for the user based on the configuration and rules. The informational messages could be, for example, popup notifications, messages, suggestions, etc., that may explain features of the interface or recommended actions. The buttons may explain the function of user interface components to aid the user to get comfortable with the interface.

At step 310, the EHR server monitors the activity of users with the user interface. For example, the EHR server tracks completion of tasks and tutorials by the user. EHR server may also monitor usage patterns and can update the user profile configuration based on detected patterns. For example, if the EHR server detects that the user regularly manually enters patient medication information but has not yet subscribed to e-prescription, the EHR server configures the user profile to suggest e-prescription to the user.

In an embodiment, step 310 also includes monitoring the activity of other users in the same practice. For example, the EHR server may detect that a user, who is an office staff member, has taken an e-billing setup tutorial, and based on that determination, the EHR server may omit suggesting the same tutorial to other users in the practice who may not be interested in initiating the e-billing setup action. However, an e-prescription tutorial may be offered to users who are doctors, but not to users who are office staff or medical assistants.

At step 312, the EHR server updates the user profile and practice configurations based on the monitored activity and task completion by the users. In an embodiment, the EHR server continuously performs method 300 as the user interacts with the user interface.

FIGS. 4A-D show screen layouts illustrating various aspects of a dynamically configured EHR user interface 400, according to an example embodiment. FIGS. 4A-D are meant to show examples of the interface as dynamically configured using the above described exemplary methods 200 and 300.

The user interface 400 includes a dashboard 410, menus 420, and dynamically generated informational messages 430.

Dashboard 410 provides an at-a-glance view of the practice. Dashboard 410 may include one or more menus 420 with selectable items to perform various functions. Furthermore, dashboard 410 can display various statistics and other information associated with the practice.

Figure 4A:
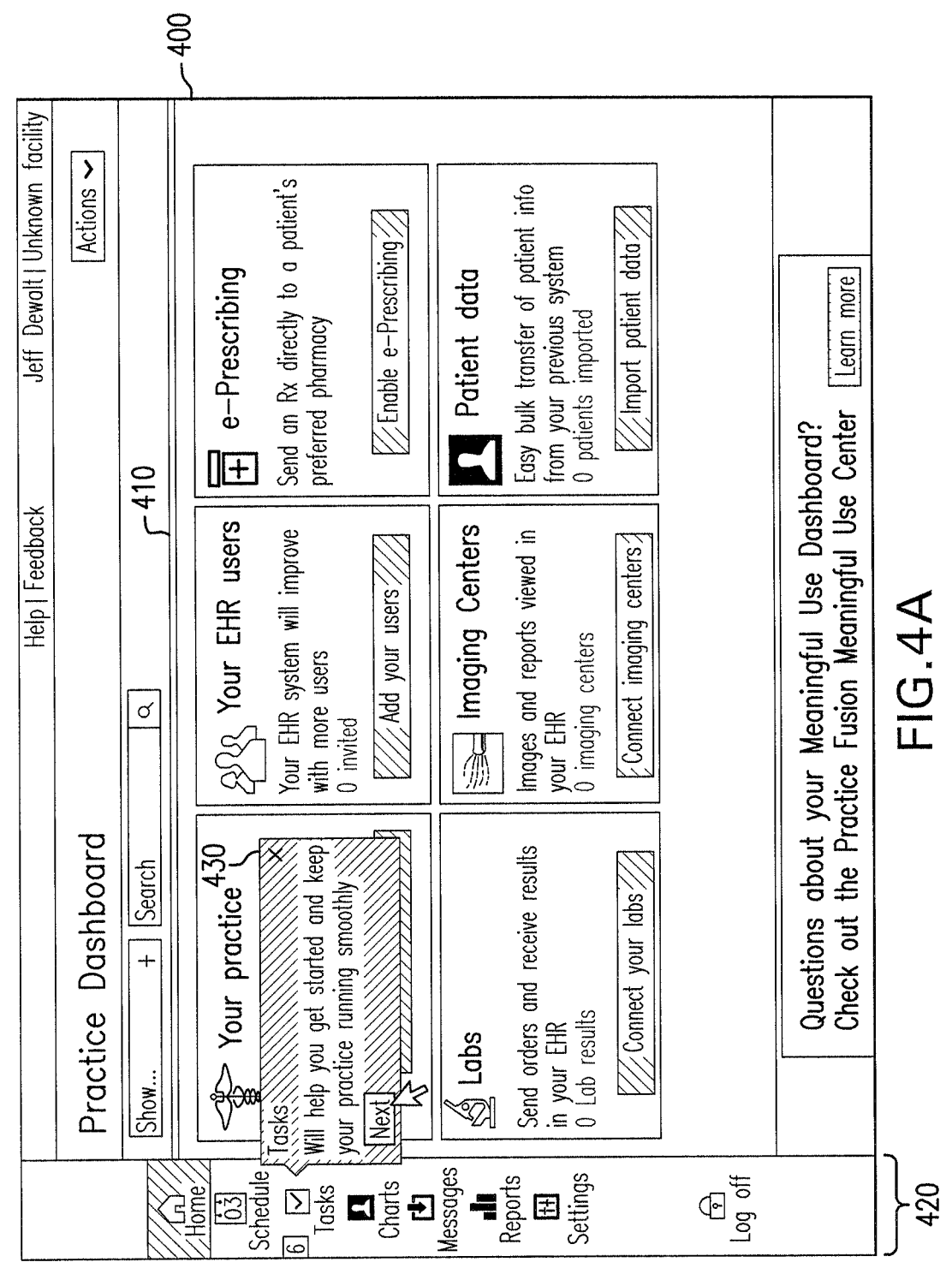

In an embodiment, dashboard 410 also includes informational messages 430, which may be dynamically generated based on the above-explained methods by, for example, an EHR system with a configurator module. As shown in FIG. 4A, a rule may specify that when a user logs in for the first time, an informational message is displayed explaining the function of the various selectable items in menus 420. As a result, the EHR server may display a series of messages 430 for a user that satisfies that rule. In the embodiment of FIG. 4, the user can click a "Next" button in message 430 to proceed to a next message explaining the function of another menu item.

Figure 4B:
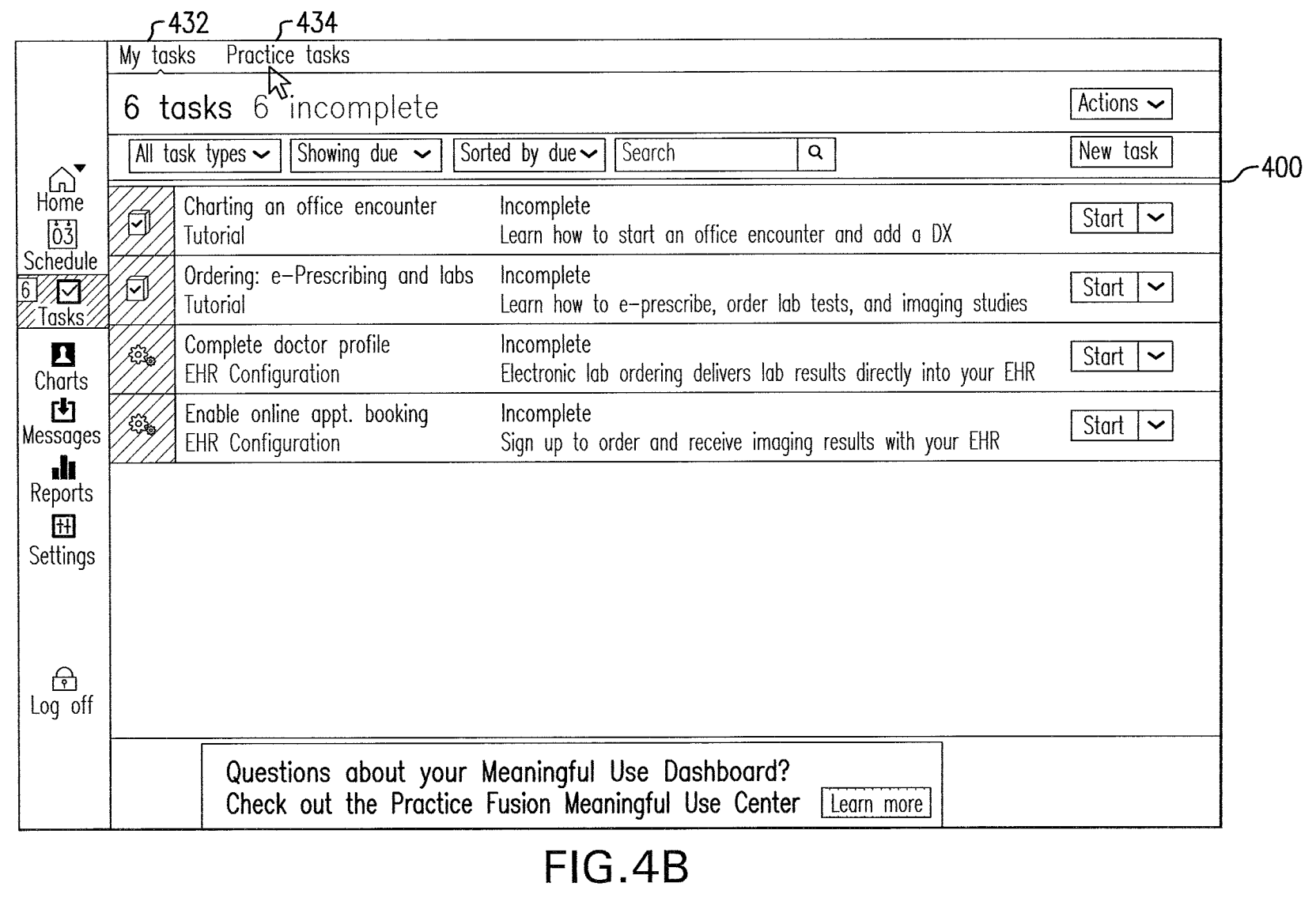

FIG. 4B shows a list of tasks for the practice user to complete, according to an example embodiment. A user may be directed to the screen of FIG. 4B when the user selects the task item in menu 420. EHR server may display different tasks for different users and practices, based on the configuration information and the rules. In an embodiment, the tasks are divided into tasks for the user (e.g., "My Tasks") or tasks for the practice (e.g., "Practice Tasks"), as shown in tabs 432 and 434. In an embodiment, user tasks are to be completed by the particular user, while Practice Tasks may be completed by any user in the practice.

FIG. 4C shows a screen displaying a tutorial of charting an office encounter, according to an example embodiment. As explained above, the EHR server may suggest that the user complete a tutorial based on the configuration information and the rules. When a user initiates a tutorial, the EHR system may present the user with an interface and messages, such as message 436, which explain various features of the interface for the user. The tutorial may direct the user to navigate through various functions of the user interface in order to teach the user how to perform charting.

FIG. 4D shows a dashboard 410 after an initial login, according to an example embodiment. The various elements of dashboard 410 may show information related to various aspects of the practice. For example, it may show how many users are part of the practice and how many of them are using the EHR system, a list of appointments, a list of tasks and tutorials to be completed, etc. The information displayed may depend on the configuration and monitored user activity. Moreover, on logins after an initial login, dashboard 410 may provide direct access to tasks that require user attention. For example, dashboard 410 may provide an option stating "2 new appointment requests" and when a user selects that option, she is taken directly to the first of the two new appointment requests for approval.

Example Computing Device

Each of the servers and modules in FIG. 1 may be implemented on the same or different computing devices in hardware, software, or any combination thereof. Such computing devices can include, but are not limited to, a personal computer, a mobile device such as a mobile phone, tablet, workstation, embedded system, game console, television, set-top box, or any other computing device. Further, a computing device can include, but is not limited to, a device having a processor and memory, including a nontransitory memory, for executing and storing instructions. The memory may tangibly embody the data and program instructions. Software may include one or more applications and an operating system. Hardware can include, but is not limited to, a processor, memory, and graphical user interface display. The computing device may also have multiple processors and multiple shared or separate memory components. For example, the computing device may be a part of or the entirety of a clustered computing environment or server farm.

Figure 5:
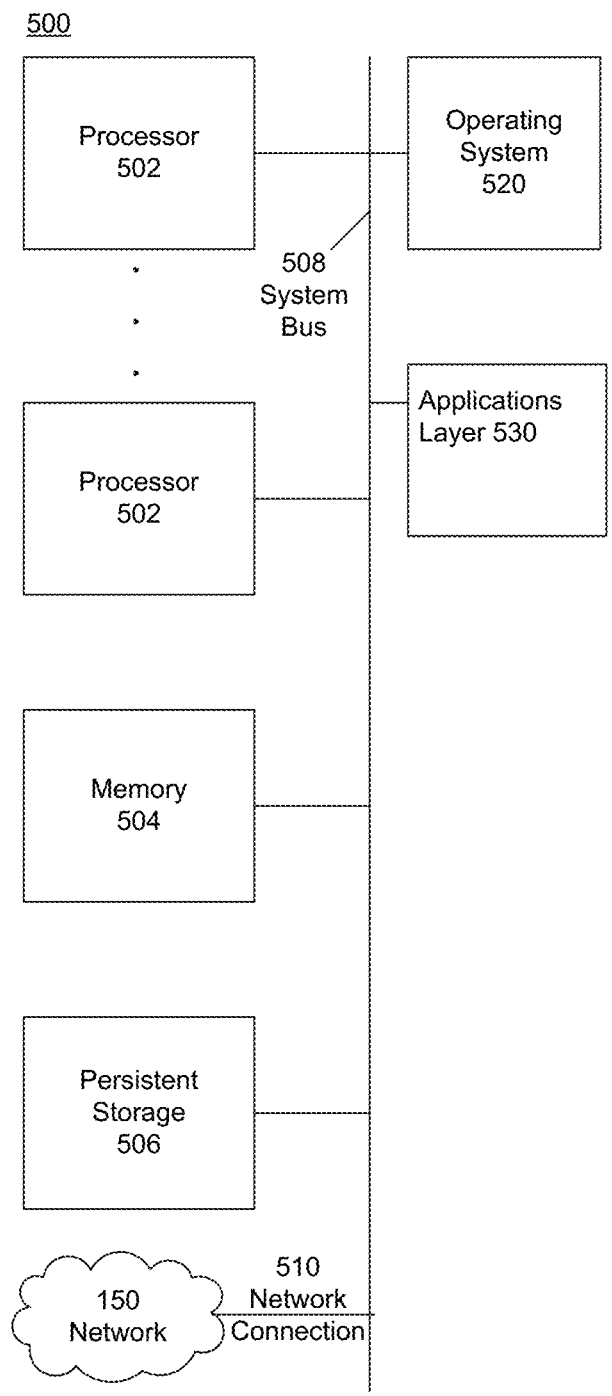
FIG. 5 is a diagram illustrating an example computing device, according to an embodiment.

An example computing device is illustrated in FIG. 5. FIG. 5 is a diagram illustrating a computing device 500 that accesses a network 150 over a network connection 510 that provides computing device 500 with telecommunications capabilities. Computing device 500 uses an operating system 520 as software that manages hardware resources and coordinates the interface between hardware and software.

In an embodiment, computing device 500 contains a combination of hardware, software, and firmware constituent parts that allow it to run an applications layer 530. Computing device 500, in embodiments, may be organized around a system bus 508, but any type of infrastructure that allows the hardware infrastructure elements of computing device 500 to communicate with and interact with each other may also be used.

Processing tasks in the embodiment of FIG. 5 are carried out by one or more processors 502. However, it should be noted that various types of processing technology may be used here, including multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors 502 may be a graphics-processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

In order to manipulate data in accordance with embodiments describe herein, processors 502 access a memory 504 via system bus 508. Memory 504 is nontransitory memory, such as random access memory (RAM). Memory 504 may include one or more levels of cache. Memory 504 has stored therein control logic (i.e., computer software) and/or data. For data that needs to be stored more permanently, processors 502 access persistent storage 506 via system bus 508. Persistent storage 506 may include, for example, a hard disk drive and/or a removable storage device or drive. A removable storage drive may be an optical storage device, a compact disc drive, flash memory, a floppy disk drive, a magnetic tape drive, tape backup device, and/or any other storage device/drive.

Processors 502, memory 504, and persistent storage 506 cooperate with operating system 520 to provide basic functionality for computing device 500. Operating system 520 provides support functionality for applications layer 530.

Network connection 510 enables computer device 500 to communicate and interact with any combination of remote devices, remote networks, remote entities, etc. For example, network connection 510 may allow computer device 500 to communicate with remote devices over network 150, which may be a wired and/or wireless network, and which may include any combination of LANs, WANs, the Internet, etc. Control logic and/or data may be transmitted to and from computer device 500 via network connection 510.

Applications layer 530 may house various modules and components. For example, EHR system 121, configurator module 122, profile database 123, rules database 124, and user interface module 125 may be included in applications layer 530 when computing device 500 is used as server 120.

It should be noted that computer-readable medium embodiments may include any physical medium which is capable of encoding instructions that may subsequently by used by a processor to implement methods described herein. Example physical media may include floppy discs, optical discs (e.g. CDs, mini-CDs, DVDs, HD-DVD, Blu-ray), hard drives, punch cards, tape drives, flash memory, or memory chips. However, any other type of tangible, persistent storage that can serve in the role of providing instructions to a processor may be used to store the instructions in these embodiments.

Comprehensive EHR System

A comprehensive EHR system includes a variety of components. Components of EHR systems vary from vendor to vendor and from setting to setting. For example, an EHR system in which embodiments of the present invention can be used may also include: (1) an electronic prescription (eRx) component, (2) a clinical laboratory component, (3) an imaging center component (4) a transfer of care component, (5) a scheduling component, (6) a billing service component, and (7) a patient portal component.

The electronic prescription component provides medical professionals capabilities to electronically generate and transmit prescriptions for patients' medications. Some EHR systems enable prescribers to view their patients' prescription benefit information at the point of care and select medications that are on formulary and covered by the patient's drug benefits. This informs physicians of potential lower cost alternatives (such as generic drugs) and reduces administrative burden of pharmacy staff and physicians related to benefit coverage.

The clinical laboratory component allows medical professionals to integrate with clinical laboratories to electronically receive and incorporate clinical laboratory tests and results into a patient's chart and create computerized provider order entry ("CPOE") clinical laboratory orders.

The imaging center component can support functionality that enables medical professionals to electronically receive and incorporate radiology laboratory test results (e.g., x-ray, ultrasound, MRI, PET/CT scan, mammography) into a patient's chart.

Medical professionals can use the transfer of care component to transmit referrals electronically to other EHR users or to non-users by facsimile. Additionally, some EHR systems support electronically creating and transmitting consolidated continuity of care documents.

The scheduling component offers functionality that allows healthcare providers to manage their appointments with an electronic schedule that can be integrated into a practice's workflow.

The billing service component offers medical professionals the ability to electronically generate and transmit superbills. Superbills are the data source for the creation of a healthcare claim. The billing service component can transmit superbills to medical billing software accounts controlled by the professionals' offices or their billing service providers. This component also allows a healthcare professional to save a superbill and transmit it to the health care professional's billing account with the billing software vendor.

The patient portal component, often called the personal health record (PHR), allows medical professionals to grant their patients an online means to view, download, and transmit their health information. This component also provides patients with the ability to book appointments, review their physicians and send and receive secure messages directly to and from their physicians.

Together, these components leverage the benefits of EHRs while mitigating the risks.

CONCLUSION

Identifiers, such as "(a)," "(b)," "(i)," "(ii)," etc., are sometimes used for different elements or steps. These identifiers are used for clarity and do not necessarily designate an order for the elements or steps.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computing system that is in network communication with several client computing devices, the computing system comprising:
a processor; and
memory storing a web-based electronic health record application (EHR) that is used by a medical service provider, wherein the EHR is configured to create and present customized graphical user interfaces (GUIs) to users of the EHR, wherein the EHR, when executed by the processor, causes the processor to perform acts comprising:
receiving, from a web browser executing on a client computing device in the client computing devices, registration information of the medical service provider, wherein the EHR registers the medical service provider with the EHR based upon the registration information;
subsequent to receiving the registration information, receiving, from the web browser executing on the client computing device in the client computing devices, profile information for a user in the medical service provider, wherein the profile information comprises an indication of a role of the user in the medical service provider;
responsive to receiving the profile information, creating a user profile for the user based upon the profile information;
subsequent to creating the user profile, identifying, in a rules database that comprises configuration rules for the EHR, a configuration rule from amongst the configuration rules, wherein the configuration rule is identified based upon the role of the user;
generating configuration information for the user profile, the configuration information specified by the configuration rule;
subsequent to generating the configuration information for the user profile, detecting that the user has logged into the EHR by way of a web browser executing on a second client computing device in the client computing devices;
responsive to detecting that the user has logged into the EHR, causing a GUI of the EHR to be displayed on a display of the second client computing device, wherein the GUI is based upon the configuration information generated for the user profile, wherein the GUI comprises visual indictors, each visual indicator assigned to a different service of the EHR that facilitates care of patients of the medical service provider;
subsequent to causing the GUI of the EHR to be displayed on the display of the client computing device, monitoring an activity of the user in the EHR, wherein the monitored activity of the user comprises a usage pattern of the EHR by the user;
determining an additional service of the EHR to recommend to the user based upon the monitored activity;
responsive to determining the additional service of the EHR to recommend to the user, causing the GUI of the EHR to be updated to include a visual indicator representing an option to use the additional service of the EHR; and
when the user indicates that the additional service is to be used, updating the configuration information based upon the user indicating that the additional service is to be used, wherein the configuration information is updated based upon a second configuration rule from the rules database, the second configuration rule corresponding to the additional service.

2. The computing system of claim 1, wherein the configuration information specifies at least one of a service to be offered to the user, a tutorial to be suggested to the user, or a task to be completed by the user.

3. The computing system of claim 1, the acts further comprising:
generating a question for the user based on a plurality of rules, wherein the configuration information is further generated based on a response by the user to the question.

4. The computing system of claim 1, the acts further comprising:
subsequent to causing the GUI of the EHR to be displayed on the display of the second client computing device, monitoring a second activity of the user in the EHR, wherein the second monitored activity of the user comprises a task completion by the user;
determining a second additional service of the EHR to recommend to the user based upon the second monitored activity;
responsive to determining the second additional service of the EHR to recommend to the user, causing the GUI of the EHR to be updated to include a second visual indicator representing an option to use the second additional service of the EHR; and
when the user indicates that the second additional service is to be used, updating the configuration information based upon the user indicating that the second additional service is to be used.

5. The computing system of claim 1, wherein the additional service is an electronic prescription service.

6. The computing system of claim 1, the acts further comprising:
causing the GUI to be updated to include a second visual indicator assigned to the additional service of the EHR.

7. The computing system of claim 1, wherein a layout of the visual indicators within the GUI is defined by the configuration information for the user profile.

8. A non-transitory computer-readable storage medium comprising instructions that, when executed by a processor, cause the processor to perform acts comprising:
receiving, from a web browser executing on a client computing device from amongst several client computing devices that are in communication with the processor, registration information of a medical service provider that is registering with an electronic health record application (EHR), wherein the EHR registers the medical service provider with the EHR based upon the registration information;
subsequent to receiving the registration information, receiving, from the web browser executing on the client computing device in the client computing devices, profile information for a user in the medical service provider, wherein the profile information comprises an indication of a role of the user in the medical service provider;

responsive to receiving the profile information, creating a user profile for the user based upon the profile information;

subsequent to creating the user profile for the user, identifying, in a rules database that comprises configuration rules for the EHR, a configuration rule from amongst the configuration rules, wherein the configuration rule is identified based upon the role of the user;

generating configuration information for the user profile, the configuration information specified by the configuration rule;

subsequent to generating the configuration information for the user profile, detecting that the user has logged into the EHR by way of a web browser executing on a second client computing device in the client computing devices;

responsive to detecting that the user has logged into the EHR, causing a graphical user interface (GUI) of the EHR to be displayed on a display of the second client computing device, wherein the GUI is based upon the configuration information generated for the user profile, wherein the GUI comprises visual indictors, each visual indicator assigned to a different service of the EHR that facilitates care of patients of the medical service provider;

subsequent to causing the GUI of the EHR to be displayed on the display of the client computing device, monitoring an activity of the user in the EHR, wherein the monitored activity of the user comprises a usage pattern of the EHR by the user;

determining an additional service of the EHR to recommend to the user based upon the monitored activity;

responsive to determining the service of the EHR to recommend to the user, causing the GUI of the EHR to be updated to include a visual indicator representing an option to use the additional service of the EHR; and when the user indicates that the additional service is to be used, updating the configuration information based upon the user indicating that the additional service is to be used, wherein the configuration information is updated based upon a second configuration rule from the rules database, the second configuration rule corresponding to the additional service.

9. The non-transitory computer-readable storage medium of claim 8, wherein the configuration information specifies at least one of a service to be offered to the user, a tutorial to be suggested to the user, or a task to be completed by the user.

10. The non-transitory computer-readable storage medium of claim 8, the acts further comprising:
generating a question for the user based on a plurality of rules, wherein the configuration information is further generated based on a response by the user to the question.

11. The non-transitory computer-readable storage medium of claim 8, the acts further comprising:
subsequent to causing the GUI of the EHR to be displayed on the display of the client computing device, monitoring a second activity of the user in the EHR, wherein the second monitored activity of the user comprises a task completion by the user;
determining a second additional service of the EHR to recommend to the user based upon the second monitored activity;

responsive to determining the second additional service of the EHR to recommend to the user, causing the GUI of the EHR to be updated to include a second visual indicator representing an option to use the second additional service of the EHR; and
when the user indicates that the second additional service is to be used, updating the configuration information based upon the user indicating that the second additional service is to be used.

12. The non-transitory computer-readable storage medium of claim 8, wherein the additional service is an electronic prescription service.

13. The non-transitory computer-readable storage medium of claim 8, the acts further comprising:
causing the GUI to be updated to include a second visual indicator assigned to the additional service of the EHR.

14. The non-transitory computer-readable storage medium of claim 8, wherein a layout of the visual indicators within the GUI is defined by the configuration information for the user profile.

15. A computer-implemented method for creating and presenting customized graphical user interfaces (GUIs) to users of an electronic health record application (EHR), the method performed by a server computing device that is in network communication with client computing devices of a medical service provider, the method comprising:
receiving, from a web browser executing on a client computing device in the client computing devices, registration information of the medical service provider, wherein the server computing device registers the medical service provider with the EHR based upon the registration information;

subsequent to receiving the registration information, receiving, from the web browser executing on the client computing device in the client computing devices, profile information for a user in the medical service provider, wherein the profile information comprises an indication of a role of the user in the medical service provider;

responsive to receiving the profile information, creating a user profile for the user based upon the profile information;

subsequent to creating the user profile, identifying, in a rules database that comprises configuration rules for the EHR, a configuration rule from amongst the configuration rules, wherein the configuration rule is identified based upon the role of the user;

generating configuration information for the user profile, the configuration information specified by the configuration rule;

subsequent to generating the configuration information for the user profile, detecting that the user has logged into the EHR by way of a web browser executing on a second client computing device in the client computing devices;

responsive to detecting that the user has logged into the EHR, causing a GUI of the EHR to be displayed on a display of the second client computing device, wherein the GUI is based upon the configuration information generated for the user profile, wherein the GUI comprises visual indictors, each visual indicator assigned to a different service of the EHR that facilitates care of patients of the medical service provider;

subsequent to causing the GUI of the EHR to be displayed on the display of the client computing device, monitoring an activity of the user in the EHR, wherein the monitored activity of the user comprises a usage pattern of the EHR by the user;

determining an additional service of the EHR to recommend to the user based upon the monitored activity;

responsive to determining the additional service of the EHR to recommend to the user, causing the GUI of the EHR to be updated to include a visual indicator representing an option to use the additional service of the EHR; and when the user indicates that the service is to be used, updating the configuration information based upon the user indicating that the additional service is to be used, wherein the configuration information is updated based upon a second configuration rule from the rules database, the second configuration rule corresponding to the additional service.

16. The method of claim 15, wherein the configuration information specifies at least one of a service to be offered to the user, a tutorial to be suggested to the user, or a task to be completed by the user.

17. The method of claim 15, further comprising:
generating a question for the user based on a plurality of rules, wherein the configuration information is further generated based on a response by the user to the question.

18. The method of claim 15, further comprising:
subsequent to causing the GUI of the EHR to be displayed on the display of the client computing device, monitoring a second activity of the user in the EHR, wherein the second monitored activity of the user comprises a task completion by the user;

determining a second additional service of the EHR to recommend to the user based upon the second monitored activity;

responsive to determining the second additional service of the EHR to recommend to the user, causing the GUI of the EHR to be updated to include a second visual indicator representing an option to use the second additional service of the EHR; and when the user indicates that the second additional service is to be used, updating the configuration information based upon the user indicating that the second additional service is to be used.

19. The method of claim 15, wherein the additional service is an electronic prescription service.

20. The method of claim 15, further comprising:
causing the GUI to be updated to include a second visual indicator assigned to the additional service of the EHR.

* * * * *